United States Patent [19]

Jeffries, III et al.

[11] Patent Number: 5,196,289

[45] Date of Patent: * Mar. 23, 1993

[54] SELECTED BLOCK PHENOLIC OLIGOMERS AND THEIR USE IN RADIATION-SENSITIVE RESIST COMPOSITIONS

[75] Inventors: Alfred T. Jeffries, III, Providence; Kenji Honda, Barrington, both of R.I.; Andrew J. Blakeney; Sobhy Tadros, both of Seekonk, Mass.

[73] Assignee: OCG Microelectronic Materials, Inc., Cheshire, Conn.

[*] Notice: The portion of the term of this patent subsequent to Feb. 23, 2010 has been disclaimed.

[21] Appl. No.: 711,350

[22] Filed: Jun. 4, 1991

Related U.S. Application Data

[63] Continuation of Ser. No. 404,138, Sep. 7, 1989, abandoned.

[51] Int. Cl.⁵ .................... G03F 7/023; G03F 7/32
[52] U.S. Cl. ......................... 430/192; 430/165; 430/193; 430/326; 528/155
[58] Field of Search ............. 430/192, 193, 165, 166, 430/326; 528/155, 156

[56] References Cited

U.S. PATENT DOCUMENTS

| | | | |
|---|---|---|---|
| 3,384,618 | 5/1968 | Imoto et al. | 260/47 |
| 3,422,068 | 1/1969 | Kreibich et al. | 260/52 |
| 4,146,739 | 3/1979 | Akutin et al. | 568/720 |
| 4,345,054 | 8/1982 | Takeda et al. | 525/480 |
| 4,377,631 | 3/1983 | Toukhy et al. | 430/192 |
| 4,555,469 | 11/1985 | Erdmann et al. | 430/192 |
| 4,642,282 | 2/1987 | Stahlhofen | 430/192 |
| 4,703,086 | 10/1987 | Yamamoto et al. | 525/133 |
| 4,731,319 | 3/1989 | Kohara et al. | 430/192 |
| 4,826,821 | 5/1989 | Clements | 514/78 |
| 4,835,204 | 5/1989 | Carfagnini | 524/291 |
| 4,837,121 | 6/1989 | Blakeney et al. | 430/165 |
| 4,876,324 | 10/1989 | Nakano et al. | 528/142 |

FOREIGN PATENT DOCUMENTS

| | | | |
|---|---|---|---|
| 273026 | 6/1988 | European Pat. Off. | |
| 59-211415 | 7/1984 | Japan | 430/192 |
| 59-184337 | 10/1984 | Japan | 430/192 |
| 60-97347 | 5/1985 | Japan | |
| 0329949 | 2/1991 | Japan | |

OTHER PUBLICATIONS

Chatterjee, S. K. "Non-Aqueous Titration of Polynuclear Phenolic Compounds: Part IV—Titration of Some High Molecular Weight Synthetic Compounds of Uniform Constitution", Jun. 1969, pp. 605-610.

Chatterjee et al. "Correlation of Composition and DP of Some 3-Component Phenolic Block Copolymers with Their Titration Curves in Nonaqueous Media", 1981, pp. 717-727.

Chatterjee et al. "Dissociation Behavior of Some Mixtures of Synthetic Phenolic Oligomers in Nonaqueous Media", 1978, pp. 1031-1039.

Chatterjee et al. "Effect of Substituents on the Composition and Dissociation Behavior or Some Four Component Phenolic Copolymers", Oct. 1981.

Chatterjee et al. "Study of Electrochemical Properties and Formation of Some Phenolic Block Copolymers", 1983, pp. 93-103.

Primary Examiner—Charles L. Bowers, Jr.
Assistant Examiner—John S. Chu
Attorney, Agent, or Firm—William A. Simons

[57] ABSTRACT

Block phenolic oligomers of the formula (I):

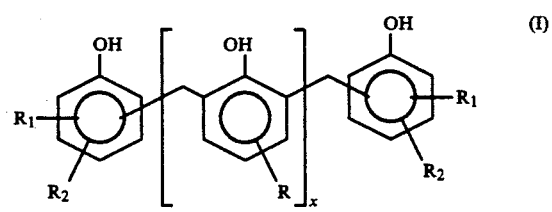

These may be reacted alone or with selected phenolic monomers during or after the formation of a phenolic novolak resin thereby said resin having at least one unit of formula (II):

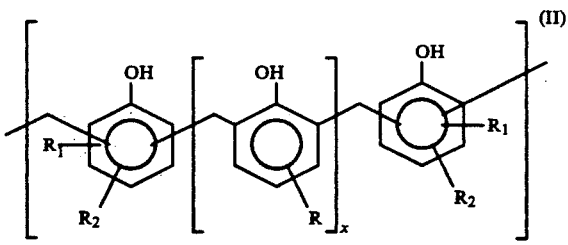

13 Claims, No Drawings

SELECTED BLOCK PHENOLIC OLIGOMERS AND THEIR USE IN RADIATION-SENSITIVE RESIST COMPOSITIONS

This application is a continuation of application Ser. No. 07/404,138, filed Sep. 7, 1989, now abandoned.

The present invention relates to selected block phenolic oligomers as novel compositions of matter. The present invention relates to selected phenolic resins containing at least one unit of such selected block phenolic oligomers. Furthermore, the present invention relates to radiation-sensitive compositions useful as positive-working photoresist compositions, particularly, those containing these phenolic resins and o-quinonediazide photosensitizers. Still further, the present invention also relates to substrates coated with these radiation-sensitive compositions as well as the process of coating, imaging and developing these radiation-sensitive mixtures on these substrates.

Photoresist compositions are used in microlithographic processes for making miniaturized electronic components such as in the fabrication of integrated circuits and printed wiring board circuitry. Generally, in these processes, a thin coating or film of a photoresist composition is first applied to a substrate material, such as silicon wafers used for making integrated circuits or aluminum or copper plates of printed wiring boards. The coated substrate is then baked to evaporate any solvent in the photoresist composition and to fix the coating onto the substrate. The baked coated surface of the substrate is next subjected to an image-wise exposure of radiation. This radiation exposure causes a chemical transformation in the exposed areas of the coated surface. Visible light, ultraviolet (UV) light, electron beam and X-ray radiant energy are radiation types commonly used today in microlithographic processes. After this image-wise exposure, the coated substrate is treated with a developer solution to dissolve and remove either the radiation-exposed or the unexposed areas of the coated surface of the substrate. In some instances, it may be desirable to bake the imaged coated substrate after the imaging step and before the developing step. This bake step is commonly called a post-exposure bake and is used to increase resolution.

There are two types of photoresist compositions—negative-working and positive-working. When negative-working photoresist compositions are exposed image-wise to radiation, the areas of the resist composition exposed to the radiation become less soluble to a developer solution (e.g. a cross-linking reaction occurs) while the unexposed areas of the photoresist coating remain relatively soluble to a developing solution. Thus, treatment of an exposed negative-working resist with a developer solution causes removal of the non-exposed areas of the resist coating and the creation of a negative image in the photoresist coating, and thereby uncovering a desired portion of the underlying substrate surface on which the photoresist composition was deposited. On the other hand, when positive-working photoresist compositions are exposed image-wise to radiation, those areas of the resist composition exposed to the radiation become more soluble to the developer solution (e.g. a rearrangement reaction occurs) while those areas not exposed remain relatively insoluble to the developer solution. Thus, treatment of an exposed positive-working resist with the developer solution causes removal of the exposed areas of the resist coating and the creation of a positive image in the photoresist coating. Again, a desired portion of the underlying substrate surface is uncovered.

After this development operation, the now partially unprotected substrate may be treated with a substrate-etchant solution or plasma gases and the like. This etchant solution or plasma gases etch the portion of the substrate where the photoresist coating was removed during development. The areas of the substrate where the photoresist coating still remains are protected and, thus, an etched pattern is created in the substrate material which corresponds to the photomask used for the image-wise exposure of the radiation. Later, the remaining areas of the photoresist coating may be removed during a stripping operation, leaving a clean etched substrate surface. In some instances, it is desirable to heat treat the remaining resist layer after the development step and before the etching step to increase its adhesion to the underlying substrate and its resistance to etching solutions.

Positive-working photoresist compositions are currently favored over negative-working resists because the former generally have better resolution capabilities and pattern transfer characteristics.

Photoresist resolution is defined as the smallest feature which the resist composition can transfer from the photomask to the substrate with a high degree of image edge acuity after exposure and development. In many manufacturing applications today, resist resolution on the order of one micron or less are necessary.

In addition, it is generally desirable that the developed photoresist wall profiles be near vertical relative to the substrate. Such demarcations between developed and undeveloped areas of the resist coating translate into accurate pattern transfer of the mask image onto the substrate.

Increased resolution has been noted in positive photoresist systems whose novolaks possess a high degree of ortho, ortho bonding. The term ortho, ortho bonding is used to refer to the location and positions of attachment of the methylene bridge between cresol nuclei. Thus, the bridge which connects two phenolic nuclei which is ortho to both phenolic hydroxyl groups is regarded as ortho, ortho.

It is thought that ortho, ortho bonding increases the interactions between the novolak and the photoactive compound in positive photoresists compared to positive photoresists containing novolaks which lack a high degree of ortho, ortho bonding in their micro- structure. Although the exact character of these interactions is speculative, e.g., hydrogen bonding, van der Waals forces, etc., there is a correlation between increased resolution and contrast observed in these positive resists whose novolaks contain a high degree of ortho, ortho bonding compared to Positive resists whose novolaks lack this high degree of ortho, ortho bonding.

The optimum number of consecutive ortho, ortho bonds necessary for optimum interaction between PAC and novolak and their dispersion throughout the novolak microstructure and molecular weight range is not known. The use of novolaks having high or complete ortho, ortho bonding in photoresists is correlated with undesired residues in the exposed and developed areas. Having the optimum number of ortho, ortho bonds distributed properly may minimize or eliminate this problem.

Accordingly, the present invention is directed to selected block phenolic oligomers of the formula (I):

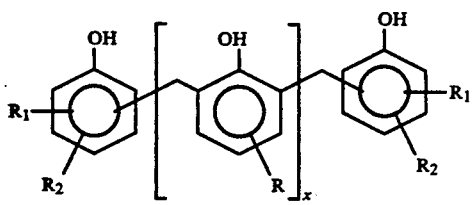 (I)

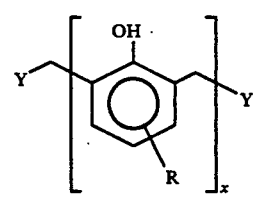 (IA)

wherein x is from 2–7;

wherein R is hydrogen, a lower alkyl having 1-4 carbon atoms or lower alkoxy group having 1-4 carbon atoms or a halogen group; and wherein $R_1$ and $R_2$ are individually selected from a hydrogen, hydroxyl, a lower alkyl group or lower alkoxy group having 1 to 4 carbon atoms or a halogen group subject to the following provisos:

(a) at least one of the positions which are ortho or para to the hydroxyls on the terminal phenolic moieties is unsubstituted, and (b) if either $R_1$ or $R_2$ is in the same position relative to the hydroxyl groups on the terminal phenolic moieties as R is to the hydroxyl on the interior phenolic moieties and the other $R_1$ or $R_2$ is hydrogen, $R_1$ or $R_2$ is not the same as R.

Moreover the present invention is directed to a Phenolic novolak binder resin comprising at least one unit of formula (II):

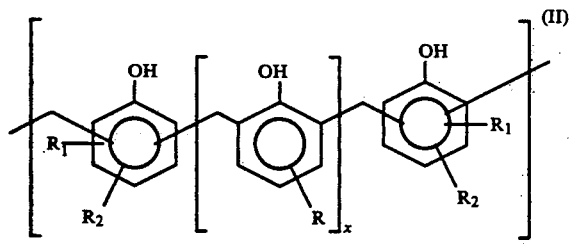 (II)

wherein x, R, $R_1$, and $R_2$ are the same as defined above.

Moreover, the present invention is directed to a radiation-sensitive composition useful as a positive photoresist comprising an admixture of o-quinonediazide compound and binder resin comprising at least one unit of the formula (II), above; the amount of said o-quinonediazide compound or compounds being about 5% to about 40% by weight and the amount of said binder resin being about 60% to 95% by weight, based on the total solid content of said radiation-sensitive composition.

Also further, the present invention encompasses said coated substrates (both before and after imaging) as novel articles of manufacture.

Still further, the present invention also encompasses the process of coating substrates with these radiation-sensitive compositions and then imaging and developing these coated substrates.

The selected block phenolic oligomers of formula (I) are made by reacting the block oligomer group (IA) having the formula:

wherein Y is a hydroxyl or a halogen and R and x are as defined above, with monomer (IB) having the formula:

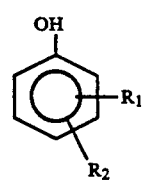 (IB)

wherein $R_1$ and $R_2$ are the same as defined above, subject to the above proviso (b) and at least two of the ortho and para positions to the hydroxyl groups in formula (IB) are unsubstituted.

Preferred R substituents on the block oligomer groups IA are hydrogen, methyl, methoxy, and chlorine. Most preferred R substituents are methyl and methoxy. Preferred x is 2–5. More preferred x is 2–4. Most preferred Y is OH.

Block oligomer groups IA may be prepared by bishydroxymethylation or bischloromethylation of the corresponding block segment. Bishydroxymethylation is conveniently carried out by reaction with excess formaldehyde or formadehyde equivalent with heat and base catalyst. Suitable base catalysts include the hydroxides of sodium, potassium, and tetramethyl ammonium. An additional water miscible solvent (e.g., methanol, ethanol) may be used to facilitate the reaction. Chloromethylation of phenolics may be carred out using chloromethyl methyl ether and a zinc chloride catalyst. Alternatively, the bischloromethyl compound may be prepared from the bishydroxymethyl compound.

Preferred monomers IB are o-cresol, m-cresol, phenol, 2-methoxyphenol, 3-methoxyphenol, 4-methoxyphenol, 2,3-xylenol, 2,5-xylenol, 3,4-xylenol, 3,5-xylenol, 2-chlorophenol, 3-chlorophenol, 4-chlorophenol, 2-chloro-3-methylphenol, 2-chloro-5-methylphenol, 3-chloro-4-methylphenol, 3-chloro-5-methylphenol, 2-ethylphenol, 3-ethylphenol, 4-ethylphenol, hydroquinone, resorcinol, 4-chlororesorcinol, 4-ethylresorcinol, 5- or 2-methylresorcinol and catechol as well as Bisphenol A. Most preferred monomers IB are o-cresol, m-cresol, and phenol.

Proviso (a) necessitates that reactive sites for condensation with formaldehyde or other aldehyde sources and an additional monomer to yield a phenolic novolak binder resin be available. Proviso (b) requires that the terminal phenolics of block oligomer I be different from the phenolic used in constructing the interior block.

In making the block phenolic oligomers of formula (I), the block oligomer group IA and monomer IB are placed in a reaction vessel along with an acid catalyst. Mole ratios of IA to IB are from about 5:1 to about 20:1. Preferred ratios of IA to IB are from about 10:1 to about 15:1. The acid catalyst concentration may range from about 0.1% to about 1%. Suitable acid catalysts include oxalic acid, maleic acid, hydrochloric acid, organic sulfonic acids, and other acid catalysts known to those skilled in the art of novolak synthesis. The reaction mixture is heated to 30°-100° C., preferably to about 40°-50° C. Reaction time will depend on the specific reactants and catalyst used. Reaction times of 2-24 hours are generally suitable. Reaction volatiles are then removed by distillation to yield the desired compounds of formula (I).

To make alkali-soluble novolak resins from the block phenolic oligomers of formula (I), a block phenolic oligomer compound or a mixture of compounds of formula (I) is reacted with at least one aldehyde source and at least one other phenolic monomeric compound of formula (III):

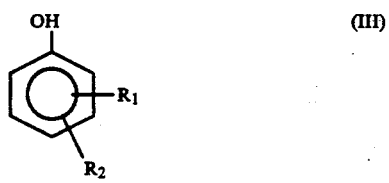

wherein $R_1$ and $R_2$ are individually selected from the group consisting of hydrogen, lower alkyl having 1-4 carbon atoms, lower alkoxy having 1-4 carbon atoms, halogen, and hydroxyl.

Suitable aldehyde sources include formalin, paraformaldehyde, formaldehyde, trioxane, acetaldehyde, alphahaloacetaledehydes such as monochloroacetaldehyde, and their respective acetals.

Preferred phenolic monomeric compounds of formula (III) include o-cresol, m-cresol, phenol, 2-methoxyphenol, 3-methoxyphenol, 4-methoxyphenol, 2,3-xylenol, 2,5-xylenol, 3,4-xylenol, 3,5-xylenol, 2-chlorophenol, 3-chlorophenol, 4-chlorophenol, 2-chloro-3-methylphenol, 2-chloro-5-methylphenol, 3-chloro-4-methylphenol, 3-chloro-5-methylphenol, 2-ethylphenol, 3-ethylphenol, 4-ethylphenol, hydroquinone, resorcinol, 4-chlororesorcinol, 4-ethylresorcinol, 5- or 2-methylresorcinol, and catechol. Most preferred monomers (III) are o-cresol, m-cresol, and phenol.

In making the present class of alkali-soluble resins, having the above-defined units of formula (I), the precursors, namely, the block copolymer oligomer of formula (I) and the phenolic monomers of formula (III) are preferably placed in a reaction vessel with an aldehyde source. The reaction mixture usually also contains an acid catalyst and may include a solvent. The acid catalysts used for making the block phenolic compounds (I) are also suitable for making these resins. Any conventional solvent used in novolak-forming reactions may be used herein. Preferred solvents are alcoholic or ethereal solvents with boiling points between 80°-220° C. The most preferred solvents are ethanol, butanol, and 1-methoxy-2-propanol or other solvents. The mixture is then preferably heated to a temperature in the range from about 60° C. to about 120° C., more preferably from about 65° C. to about 95° C., for the novolak-forming condensation polymerization reaction to occur. If an aqueous medium is used instead of an organic solvent, the reaction temperature is usually maintained at reflux, e.g. about 95° C. to 110° C. The reaction time will depend on the specific reactants used and the ratio of aldehyde source to phenolic monomers. The mole ratio of aldehyde source to total phenolic moieties is generally less than about 1:1. Reaction times from 3 to 20 hours are generally suitable.

The above-discussed resins of the present invention may be mixed with photoactive compounds to make radiation- sensitive mixtures which are useful as positive acting photoresists. The preferred class of photoactive compounds (sometimes called sensitizers) is o-quinonediazide compounds particularly esters derived from polyhydric phenols, alkyl-polyhydroxyphenones, aryl-polyhydroxyphenones, and the like which can contain up to six or more sites for esterification. The most preferred o-quinonediazide esters are derived from o-naphthoquinone-(1,2)-diazide-4-sulfonic acid and o-naphthoquinone-(1,2)-diazide-5-sulfonic acid.

Specific examples include resorcinol 1,2-naphthoquinonediazide-4-sulfonic acid esters; pyrogallol 1,2-naphthoquinonediazide-5-sulfonic acid esters, 1,2-quinonediazidesulfonic acid esters of (poly)hydroxyphenyl alkyl ketones or (poly)hydroxyphenyl aryl ketones such as 2,4-dihydroxyphenyl propyl ketone 1,2-benzoquinonediazide-4-sulfonic acid esters, 2,4,dihydroxyphenyl hexyl ketone 1,2-naphthoquinonediazide-4-sulfonic acid esters, 2,4-dihydroxybenzophenone 1,2-naphthoquinonediazide-5-sulfonic acid esters, 2,3,4-trihydroxyphenyl hexyl ketone, 1,2-naphthoquinonediazide-4-sulfonic acid esters, 2,3,4-trihydroxybenzophenone 1,2-naphthoquinonediazide-4-sulfonic acid esters, 2,3,4-trihydroxybenzophenone 1,2-naphthoquinonediazide-5-sulfonic acid esters, 2,4,6-trihydroxybenzophenone 1,2-naphthoquinonediazide-4-sulfonic acid esters, 2,4,6-trihydroxybenzophenone 1,2-naphthoquinone-diazide-5-sulfonic acid esters, 2,3,4,4'-tetra- hydroxy-benzophenone 1,2-naphthoquinonediazide-5-sulfonic acid esters, 2,3,4,4'-tetrahydroxy-benzophenone 1,2-naphthoquinonediazide-4-sulfonic acid esters, 2,2',3,4',6'-pentahydroxybenzophenone 1,2-naphthoquinonediazide-5-sulfonic acid esters and 2,3,3',4,4',5'-hexahydroxybenzophenone 1,2-naphthoquinonediazide-5-sulfonic acid esters; 1,2-quinonediazidesulfonic acid esters of bis[(poly)hydroxyphenyl] alkanes such as bis(p-hydroxyphenyl)methane 1,2-naphthoquinonediazide-4-sulfonic acid esters, bis(2,4-dihydroxyphenyl)methane 1,2-naphthoquinonediazide-5-sulfonic acid esters, bis(2,3,4-trihydroxyphenyl)methane 1,2-naphthoquinonediazide-5-sulfonic acid esters, 2,2-bis(p-hydroxyphenyl)propane 1,2-naphthoquinonediazide-4-sulfonic acid esters, 2,2-bis(2,4-dihydroxyphe 1,2-naphthoquinone-diazide-5-sulfonic acid esters and 2,2-bis(2,3,4-trihydroxyphenyl)propane 1,2-naphthoquinonediazide-5-sulfonic acid esters. Besides the 1,2-quinonediazide compounds exemplified above, there can also be used the 1,2-quinonediazide compounds described in J. Kosar, "Light-Sensitive Systems", 339-352 (1965), John Wiley & Sons (New York) or in S. DeForest, "Photoresist", 50, (1975), Mac-Graw-Hill, Inc. (New York). In addition, these materials may be used in combinations of two or more. Further, mixtures of substances formed when less than all esterification sites present on a particular polyhydric phenol, alkyl-polyhydroxyphenone, aryl-polyhydroxyphenone and the like have combined with o-quinonediazides may be effectively utilized in positive acting photoresists.

Of all the 1,2-quinonediazide compounds mentioned above, 1,2-naphthoquinonediazide-5-sulfonic acid di-, tri-, tetra-, penta- and hexa-esters of polyhydroxy compounds having at least 2 hydroxyl groups, i.e. about 2 to 6 hydroxyl groups, are most preferred.

Among these most preferred 1,2-naphthoquinone-5-diazide compounds are 2,3,4-trihydroxybenzophenone 1,2-naphthoquinonediazide-5-sulfonic acid esters, and 2,2',4,4'-tetra-hydroxybenzophenone 1,2-naphthoquinonediazide-5-sulfonic acid esters. These 1,2-quinonediazide compounds may be used alone or in combination of two or more.

The proportion of the sensitizer compound in the radiation-sensitive mixture may preferably range from about 5 to about 40%, more preferably from about 10 to about 25% by weight of the non-volatile (e.g. non-solvent) content of the light-sensitive mixture. The proportion of total binder resin of this present invention in the light-sensitive mixture may preferably range from about 60 to about 95%, more preferably, from about 75 to 90% of the non-volatile (e.g. excluding solvents) content of the light-sensitive mixture.

These radiation-sensitive mixtures may also contain conventional photoresist composition ingredients such as other resins, solvents, actinic and contrast dyes, anti-striation agents, plasticizers, speed enhancers, and the like. These additional ingredients may be added to the binder resin and sensitizer solution before the solution is coated onto the substrate.

Other binder resins may also be added beside the resins of the present invention mentioned above. Examples include phenolic-formaldehyde resins, cresol-formaldehyde resins, phenol-cresol-formaldehyde resins and polyvinylphenol resins commonly used in the photoresist art. Chloroacetaldehyde and other aldehyde sources may be used instead of formaldehyde for making these optional resins. If other binder resins are present, they will replace a portion of the binder resins of the present invention. Thus, the total amount of the binder resin in the radiation-sensitive composition will be from about 60% to about 95% by weight of the total non-volatile solids content of the radiation-sensitive composition.

The resins and sensitizers may be dissolved in a solvent or solvents to facilitate their application to the substrate. Examples of suitable solvents include methoxyacetoxy propane, ethyl cellosolve acetate, n-butyl acetate, diglyme, ethyl lactate, ethyl 3-ethoxy propionate, propylene glycol alkyl ether acetates, or mixtures thereof and the like. The preferred amount of solvent may be from about 50% to about 500%, or higher, by weight, more preferably, from about 100% to about 400% by weight, based on combined resin and sensitizer weight.

Actinic dyes help provide increased resolution on highly reflective surfaces by inhibiting back scattering of light off the substrate. This back scattering causes the undesirable effect of optical notching, especially on a substrate topography. Examples of actinic dyes include those that absorb light energy at approximately 400–460 nm [e.g. Fat Brown B (C.I. No. 12010); Fat Brown RR (C.I. No. 11285); 2-hydroxy-1,4-naphthoquinone (C.I. No. 75480) and Quinoline Yellow A (C.I. No. 47000)] and those that absorb light energy at approximately 300–340 nm [e.g. 2,5-diphenyloxazole (PPO-Chem. Abs. Reg. No. 92-71-7) and 2-(4-biphenyl)-6-phenylbenzoxazole (PBBO-Chem. Abs. Reg. No. 17064-47-0)]. The amount of actinic dyes may be up to ten percent weight levels, based on the combined weight of resin and sensitizer.

Contrast dyes enhance the visibility of the developed images and facilitate pattern alignment during manufacturing. Examples of contrast dye additives that may be used together with the light-sensitive mixtures of the present invention include Solvent Red 24 (C.I. No. 26105), Basic Fuchsin (C.I. 42514), Oil Blue N (C.I. No. 61555) and Calco Red A (C.I. No. 26125) up to ten percent weight levels, based on the combined weight of resin and sensitizer.

Anti-striation agents level out the photoresist coating or film to a uniform thickness. Anti-striation agents may be used up to five percent weight levels, based on the combined weight of resin and sensitizer. One suitable class of anti-striation agents is nonionic silicon-modified polymers. Nonionic surfactants may also be used for this purpose, including, for example, nonylphenoxy poly(ethyleneoxy) ethanol; octylphenoxy (ethyleneoxy) ethanol; and dinonyl phenoxy poly(ethyleneoxy) ethanol.

Plasticizers improve the coating and adhesion properties of the photoresist composition and better allow for the application of a thin coating or film of photoresist which is smooth and of uniform thickness onto the substrate. Plasticizers which may be used include, for example, phosphoric acid tri-(B-chloroethyl)-ester; stearic acid; dicamphor; polypropylene; acetal resins; phenoxy resins; and alkyl resins up to ten percent weight levels, based on the combined weight of resin and sensitizer.

Speed enhancers tend to increase the solubility of the photoresist coating in both the exposed and unexposed areas, and thus, they are used in applications where speed of development is the overriding consideration even though some degree of contrast may be sacrificed, i.e. in positive resists while the exposed areas of the photoresist coating will be dissolved more quickly by the developer, the speed enhancers will also cause a larger loss of photoresist coating from the unexposed areas. Speed enhancers that may be used include, for example, picric acid, nicotinic acid or nitrocinnamic acid at weight levels of up to 20%, based on the combined weight of resin and sensitizer.

The prepared radiation-sensitive resist mixture, can be applied to a substrate by any conventional method used in the photoresist art, including dipping, spraying, whirling and spin coating. When spin coating, for example, the resist mixture can be adjusted as to the percentage of solids content in order to provide a coating of the desired thickness given the type of spinning equipment and spin speed utilized and the amount of time allowed for the spinning process. Suitable substrates include silicon, aluminum or polymeric resins, silicon dioxide, doped silicon dioxide, silicon resins, gallium arsenide, silicon nitride, tantalum, copper, polysilicon, ceramics and aluminum/copper mixtures.

The photoresist coatings produced by the above described procedure are particularly suitable for application to thermally grown silicon/silicon dioxide-coated wafers such as are utilized in the production of microprocessors and other miniaturized integrated circuit components. An aluminum/aluminum oxide wafer can be used as well. The substrate may also comprise various polymeric resins especially transparent polymers such as polyesters and polyolefins.

After the resist solution is coated onto the substrate, the coated substrate is baked at approximately 70° C. to 125° C. until substantially all the solvent has evaporated and only a uniform light-sensitive coating remains on the substrate.

The coated substrate can then be exposed to radiation, especially ultraviolet radiation, in any desired exposure pattern, produced by use of suitable masks, negatives, stencils, templates, and the like. Conventional imaging process or apparatus currently used in processing photoresist-coated substrates may be employed with the present invention. In some instances, a post-exposure bake at a temperature about 10° C. higher than the soft bake temperature is used to enhance image quality and resolution.

The exposed resist-coated substrates are next developed in an aqueous alkaline developing solution. This solution is preferably agitated, for example, by nitrogen gas agitation. Examples of aqueous alkaline developers include aqueous solutions of tetramethylammonium hydroxide, sodium hydroxide, potassium hydroxide, ethanolamine, choline, sodium phosphates, sodium carbonate, sodium metasilicate, and the like. The preferred developers for this invention are aqueous solutions of either alkali metal hydroxides, phosphates or silicates, or mixtures thereof, or tetramethylammonium hydroxide.

Alternative development techniques such as spray development or puddle development, or combinations thereof, may also be used.

The substrates are allowed to remain in the developer until all of the resist coating has dissolved from the exposed areas. Normally, development times from about 10 seconds to about 3 minutes are employed.

After selective dissolution of the coated wafers in the developing solution, they are preferably subjected to a deionized water rinse to fully remove the developer or any remaining undesired portions of the coating and to stop further development. This rinsing operation (which is part of the development process) may be followed by blow drying with filtered air to remove excess water. A post-development heat treatment or bake may then be employed to increase the coating's adhesion and chemical resistance to etching solutions and other substances. The post-development heat treatment can comprise the baking of the coating and substrate below the coating's thermal deformation temperature.

In industrial applications, particularly in the manufacture of microcircuitry units on silicon/silicon dioxide-type substrates, the developed substrates may then be treated with a buffered, hydrofluoric acid etching solution or plasma gas etch. The resist compositions of the present invention are believed to be resistant to a wide variety of acid etching solutions or plasma gases and provide effective protection for the resist-coated areas of the substrate.

Later, the remaining areas of the photoresist coating may be removed from the etched substrate surface by conventional photoresist stripping operations.

The present invention is further described in detail by means of the following examples. All parts and percentages are by weight unless explicitly stated otherwise.

EXAMPLE 1

2,6-Bis[(2-hydroxy-5-methylphenyl)methyl]-4-methylphenol (o-cresol trimer) (block oligomer precursor)

A 5 liter three-necked flask was equipped with a mechanical stirring apparatus and a thermometer. The flask was charged with p-cresol (2391.1 g, 22 mole), which had been warmed to 40°-45° C., and concentrated HCl (47.3 g, 0.47 mole). 2,6-Bis(hydroxymethyl)-p-cresol (371.9 g, 2.2 mole) was added portionwise over a 15-20 minute period to the stirred reaction mixture. The temperature was controlled to a maximum temperature range of 50°-55° C. The reaction mixture was stirred for an additional 2 hours (40°-45° C. after cooling from 50°-55° C.).

The reaction mixture was transferred to a 12 liter flask. 3320 ml of toluene was added and the stirred slurry was heated to 55°-60° C. After stirring for 15 minutes, the warm slurry was filtered and the collected solid washed with 200 ml toluene. The solid was reslurried with 3320 ml toluene in the 12 liter flask and the process repeated.

The product and 4 liters of glacial acetic acid were placed in the 12 liter flask, heated to 115° C. to dissolve the product, and then allowed to cool overnight. The precipitated solid was collected by filtration and crushed. The product was then vacuum dried overnight at 40°-45° to yield 428.8 g (56%) p-cresol trimer (greater than 95% by HPLC).

EXAMPLE 2

3,3'-[(2-Hydroxy-5-methyl-1,3-benzene)dimethylene]-bis[2-hydroxy-5-benzenemethanol] (p-cresol trimer bismethylol) (block oligomer precursor)

KOH (102.22 g of 85%, 1.55 moles uncorrected) was dissolved in 410 g deionized water and transferred to a 5 liter three-necked flask equipped with mechanical stirrer, thermometer and condenser. MeOH (410 ml) and p-cresol trimer (348 g, 1 mole) were then added and the mixture stirred until dissolution occurred. The solution was cooled to 20°-25° C. and formalin (2 liters of 36% formaldehyde) was added. After stirring for 10 minutes, the reaction mixture was heated to 50° C. and held there for 24 hours or until HPLC analysis indicated product formation was >90%.

The warm reaction was filtered to remove suspended solids. The filtrate was transferred to a 12 liter flask and 5 liters of deionized water added. Glacial acetic acid (120 ml) was added with vigorous stirring to lower the pH from about 10.7 to about 4.9. n-Butanol (2.5 liters) was added to the stirred, viscous slurry while maintaining the temperature at about 50° C. to dissolve the crude product. After stirring for 10 minutes, the phases were allowed to separate and the bottom aqueous phase was discarded. The top phase was mixed with 1 liter of water, and heated to 70° C. while stirring to break up an emulsion. The two phases were separated while warm and the top phase (butanol solution) was retained.

The butanol solution was allowed to cool to room temperature and then to 0°-5° C. overnight. The product was collected by filtration, washed with 1 liter of deionized water, suction dried, and then vacuum dried at 40°-45° C. to yield 206.95 g (54.5%) of product (greater than 95% pure).

EXAMPLE 3 p-Cresol Trimer Endcapped With m-Cresol (Oligomer 1)

A one liter three-neck flask was fitted with a mechanical stirring apparatus and a thermometer and charged with m-cresol (432 g, 4 mole), and concentrated HCl (8.44 g, about 0.084 mole). 3,3'-[(2-Hydroxy-5-methyl-1,3-benzene)dimethylene]bis[2-hydroxy-5-benzenemethanol] (p-cresol trimer bismethylol from Example 2) (152 g, 0.4 mole) was added in small portions over about 15 minutes keeping the reaction mixture temperature <45° C. with a water bath. The solution was then maintained at 40°-45° C. for two hours using an oil bath. The oil bath temperature was increased to 200° C. and a gradually increasing vacuum applied to remove reaction volatiles and excess m-cresol. After reaching maximum vacuum (about 20 millibar), the reaction mixture was heated for an additional hour to ensure removal of the unreacted m-cresol. A yield of 207 g (92.4%) was obtained. HPLC analysis showed the presence of 5-6 primary products (isomers). GPC analysis indicated the presence of about 10% higher molecular weight species.

EXAMPLE 4

Preparation of p-Cresol Trimer Block Copolymer Novolaks

A 250 ml three-necked flask was equipped with a reflux condenser and mechanical stirrer. The flask was charged with Oligomer 1 (Example 3) m-cresol, and 1-methoxy-2-propanol (solvent) and stirred until dissolution was completed (see Table I). Oxalic acid dihydrate catalyst (1 percent by weight of total reactants) dissolved in 3 ml water and m-cresol were then added. The reaction mixture was refluxed for 16-17 hours at about 100° C.

The solution was heated to 220° C. to distill reaction volatiles over about a one hour time period. A gradually increasing vacuum (down to about 3 millibar) was applied over the course of 1.5-2 hours to remove residual m-cresol. Yields are shown in Table I.

TABLE I

| Example | m-cresol (g) | Oligomer 1 (g) | 37% CH$_2$O (g) | CH$_2$O/ Reactants Molar Ratio | Solvent (g) | Yield (g) |
| --- | --- | --- | --- | --- | --- | --- |
| 4a | 22.7 | 17.67 | 9.76 | 0.5:1 | 48.15 | 33.2 |
| 4b | 22.71 | 17.67 | 11.71 | 0.6:1 | 52.08 | 35.9 |
| 4c | 22.71 | 17.67 | 13.66 | 0.7:1 | 45.42 | 37.3 |
| 4d | 19.46 | 17.67 | 10.24 | 0.6:1 | 41.11 | 41.4 |
| 4e | 25.94 | 17.67 | 13.17 | 0.6:1 | 47.80 | 32.6 |

EXAMPLE 5

3,3'-Methylenebis[2-hydroxy-5-methylbenzenemethanol] (p-cresol dimer bismethylol) (block oligomer precursor)

NaOH (160 g of 50% NaOH, 2 moles) was dissolved in 200 g deionized water and transferred to a 2 liter three-necked flask equipped with mechanical stirrer, thermometer and condenser. p-Cresol dimer (228 g, 1 mole) was then added and the mixture stirred until dissolution occurred. The solution was cooled to 45° C. and formalin (1 liter of 36% formaldehyde) was added. The reaction mixture was stirred at 40° C. for 16 hours.

The reaction mixture was transferred to a 12 liter flask and 3750 ml of deionized water added. The warm reaction mixture was quickly filtered to remove suspended solids. The collected solid was washed with warm water and refiltered. The filtrates were combined and allowed to cool to room temperature. The precipitate was collected by filtration and transferred to a 4 liter beaker. n-Butanol (1 liter) and glacial acetic acid (100 ml) were added and the slurry heated with stirring to 50°-60° C. to dissolve the crude product. The aqueous bottom layer was separated and discarded. The n-butanol layer was allowed to cool overnight at 0-5° C. The precipitate was collected by filtration and vacuum dried at 40°-45° C. to yield 94.5 g (32%) product.

A second crop yielded an additional 45.8 g (20%) of product.

EXAMPLE 6 m-Cresol Endcapped p-Cresol Dimer

A 500 mL three-neck flask was fitted with a mechanical stirring apparatus and a thermometer and charged with m-cresol (216.26 g, 2 moles), and concentrated HCl (4.22 g, about 0.044 moles). 3,3'-methylenebis[(2-hydroxy-5-methylbenzene)methanol] (p-cresol dimer bismethylol from Example 5) (57.67 g, 0.2 moles) was added in small portions over about 10 minutes keeping the reaction mixture temperature <45° C. with a water bath. The solution was then maintained at 40°-45° C. for 2.3 hours. The oil bath temperature was increased to 200° C. and a gradually increasing vacuum applied to remove reaction volatiles and excess m-cresol. After reaching maximum vacuum (about 200 millibar), the reaction mixture temperature was increased to 220° C. and the reaction mixture heated for an additional 0.5 hour to ensure removal of the unreacted m-cresol. A yield of 91.2 g (97%) was obtained.

EXAMPLE 7

Preparation of p-Cresol Dimer Block Copolymers p-Cresol dimer block copolymers may be prepared according to the general procedure described in Example 4 using proportions shown in Table II.

TABLE II

| Example | m-cresol (g) | Oligomer 2 (g) | 37% CH2O (g) | Solvent (g) |
| --- | --- | --- | --- | --- |
| 7a | 10.8 | 23.43 | 7.3 | 40.54 |
| 7b | 16.22 | 23.43 | 9.74 | 46.73 |
| 7c | 27.04 | 23.43 | 14.61 | 59.09 |
| 7d | 37.84 | 23.43 | 19.48 | 71.42 |

EXAMPLE 8 p-Cresol Pentamer

A 250 mL three-neck flask is fitted with a mechanical stirring apparatus and a thermometer and charged with p-cresol (16.8 g, 0.155 mole) and concentrated HCl (0.21 g, about 0.0022 mole). 3,3'-[2-Hydroxy-5-methyl-1,3-benzene)dimethylene] bis[2-hydroxy-5-benzenemethanol] (2.91 g, 0.0102 mole)(p-cresol trimer bismethylol from Example 2) is added in small portions over about 15 minutes keeping the reaction mixture temperature <45° C. with a water bath. The solution is then maintained at 40°-45° C. for two hours. The oil bath temperature is increased to 200° C. and a gradually increasing vacuum applied to remove reaction volatile and excess p-cresol. After reaching maximum vacuum (about 20 millibar), the reaction mixture is heated for an additional hour to ensure removal of the unreacted p-cresol.

EXAMPLE 9 p-Cresol Pentamer Bismethylol

The p-cresol pentamer bismethylol may be prepared according to the procedure used in Example 2 for the p-cresol trimer bismethylol.

EXAMPLE 10 m-Cresol Encapped c-Cresol Pentamer (Oligomer 3)

m-Cresol endcapped p-cresol pentamer may be prepared according to the procedure used in Example 3 for the m-cresol endcapped p-cresol trimer.

EXAMPLE 11

Preparation of p-Cresol Pentamer Block Copolymers p-Cresol pentamer block copolymers may be prepared according to the procedure used in Example 4 using proportions shown in Table III.

TABLE III

| Example | m-cresol (g) | Oligomer 3 (g) | CH2 (g) | Solvent (g) |
|---------|--------------|----------------|---------|-------------|
| 11a     | 32.44        | 23.43          | 17.05   | 67.16       |
| 11b     | 43.26        | 23.43          | 21.92   | 80.07       |
| 11c     | 54.02        | 23.43          | 26.78   | 92.9        |

COMPARISON EXAMPLE 1 m-/p-Cresol Novolak

To a 5 liter three-neck round-bottom flask fitted with a mechanical stirring apparatus, a condenser, and a thermometer was added a mixture of m/p-cresols (40/60 m/p 2004.6 g, 18.537 mole) 37% formalin solution (992 g of 37% solution, 12.37 moles). The solution was heated in an oil bath at 95° C. and to the mixture was added oxalic acid dihydrate (20.0 g) in hot water (27 mL). After 15 minutes, the reaction temperature was raised to 110° C. and maintained at this temperature for 15 hours. The reaction temperature was then raised to 200° C. over two hours. During this time, the water and excess formaldehyde were removed by atmospheric distillation. The temperature was held at 200° C. for an additional two hours. The reaction was subjected to a gradually increasing vacuum at 200° C. and maintained at 200° C. for two hours to remove substantially all of the unreacted cresol monomers. The molten novolak was poured onto an aluminum foil tray. The yield was about 1500 g. This novolaks molecular weight by gel permeation chromatography was 7350.

Preparation of Photoresist Formulations

Photoresist formulations were prepared by dissolving in ethyl lactate three parts by weight of some of the alkali soluble resins of Example 4 (see Table 1) and the comparison resin of comparison Example 1 with one part photoactive compound prepared by condensation of 1 mole 2,3,4,4'-tetrahydroxy-benzophenone with 2.75 moles o-naphthoquinone-(1,2)diazide-5-sulfonic acid chloride. The resist solutions were filtered through an 0.2 micron pore size filter.

Photoresist Processing

A. Photoresist Coatings

Photoresist solutions prepared above were spin-coated onto four inch silicon wafers, which had been primed with hexamethyldisilazane (HMDS). The coated wafers were soft baked on a hot plate for 50 seconds at 110° C. Uniform coatings, of about 1.2 micron in thickness were obtained by spinning at velocities ranging from 4,000 to 6,000 RPM for 30 seconds, depending upon the solution viscosity. If necessary, the solids contents of the resist formulation were adjusted to fit this spin speed range.

B. Exposure of Photoresist Coatings

Photoresist coatings were exposed on a Canon G line step and repeat exposure tool equipped with a 0.43 numerical aperture lens. This exposure tool provides a narrow spectral output at 436 nm.

C. Development of Exposed Photoresist Coatings

The exposed photoresist coatings were puddle developed using a 2.38 percent weight percent tetramethyl ammonium hydroxide aqueous developer solution in a two second spray and 58 second dwell cycle followed by rinsing and spin drying.

D. Photoresist Performance Evaluations

The photoresist formulations were evaluated for photospeed; line and space resolution; scum; and profile.

The photoresists of Example 4 exhibited better profiles than the comparison resist. The Example 4 resists also exhibited similar photospeeds. The line and space resolution of the optimized comparison resist was about 0.65 microns, whereas the resolution of the unoptimized Example 4 resist was about 0.8-1 microns. The comparison resist showed no scum, whereas the resolution of Example 4 resists were limited by some scum. It is believed that resolution and objectionable scum in the Example 4 resist could be improved by adjustments in the formulation (i.e., more or less photoactive compound or use of different photoactive compound). Changes in the photoresist processing conditions are expected to improve performance characteristics.

What is claimed is:

1. A radiation-sensitive composition comprising an admixture of at least one radiation-sensitive o-quinonediazide compound and a block copolymer binder resin comprising the reaction product of:

(1) a block phenolic oligomer having a unit of formula (II):

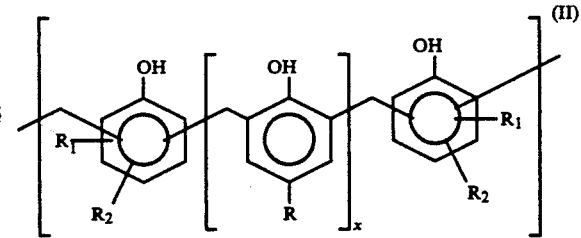

wherein x=2 to 5; wherein R is hydrogen a lower alkyl or lower alkoxy group having 1-4 carbon atoms or a halogen; wherein $R_1$ and $R_2$ are individually selected from a hydrogen, a hydroxyl, a lower alkyl group or lower alkoxy having 1 to 4 carbon atoms or a halogen group subject to the following provisos:

(a) at least one ortho- or para-position to the hydroxyls on both terminal phenolic moieties is unsubstituted;

(b) the terminal phenolic moieties are different from the phenolic moiety used to construct the interior block; with (2) at least one aldehyde source and at least one other phenolic monomeric compound having formula (III):

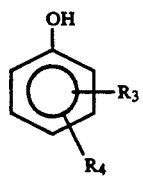

wherein $R_3$ and $R_4$ are individually selected from the group consisting of hydrogen, lower alkyl having 1–4 carbon atoms, halogen, and hydroxyl; wherein said block phenolic oligomer units constitute from about 5% to about 70% by weight of said binder resin; and wherein the amount of said o-quinonediazide compound or compounds being about 5% to about 40% by weight and the amount of said binder resin being about 60% to 95% by weight, based on the total solids content of said radiation-sensitive composition.

2. The radiation-sensitive composition of claim 1 wherein R is methyl group; $R_1$ is a methyl group, and $R_2$ is a hydrogen and x=2 to 4.

3. The radiation-sensitive composition of claim 1 wherein R is a chloro group; $R_1$ is a methyl group, and $R_2$ is a hydrogen and x=2 to 4.

4. The radiation-sensitive composition of claim 1 wherein said o-quinonediazide compound or compounds are present in the amount of about 10% to about 25% by weight, based on the total solids content of said radiation-sensitive composition, and said binder resin is present in the amount of about 75% to about 90% by weight, based on the total solids content of said radiation-sensitive composition.

5. The radiation-sensitive composition of claim 1 wherein said o-quinonediazide compound or compounds are selected from the o-naphthoquinone-(1,2)-diazide-4-sulfonic acid esters and o-naphthoquinone-(1,2)-diazide-5-sulfonic acid esters.

6. The radiation-sensitive composition of claim 5 wherein said esters are derived from polyhydric phenols, alkyl-polyhydroxyphenones and aryl-polyhydroxyphenones and mixtures thereof.

7. The radiation-sensitive composition of claim 6 wherein said esters are selected from the group consisting of polyhydroxybenzophenones and polyhydroxyacetophenones and mixtures thereof.

8. The radiation-sensitive composition of claim 1 wherein said binder resin has a molecular weight of about 500 to about 25,000.

9. The radiation-sensitive composition of claim 1 wherein said units of formula (II) represent about 30% to about 70% by weight of the said binder resin.

10. The radiation-sensitive composition of claim 1 further comprising at least one substance selected from solvents, actinic and visual contrast dyes, plasticizers, anti-striation agents and speed enhancers.

11. A coated substrate comprising a substrate coated with a film of a radiation-sensitive composition comprising an admixture of at least one radiation-sensitive o-quinonediazide compound and a block copolymer binder resin comprising the reaction product of
(1) a block phenolic oligomer having a unit of formula (II):

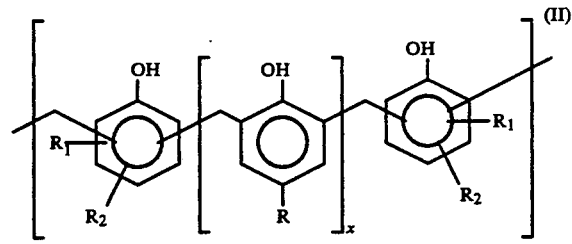

wherein x=2 to 5; wherein R is hydrogen a lower alkyl or lower alkoxy group having 1–4 carbon atoms or a halogen; wherein $R_1$ and $R_2$ are individually selected from a hydrogen, a hydroxyl, a lower alkyl group or lower alkoxy having 1 to 4 carbon atoms or a halogen group subject to the following provisos:
(a) at least one ortho- or para-position to the hydroxyls on both terminal phenolic moieties is unsubstituted;
(b) the terminal phenolic moieties are different from the phenolic moiety used to construct the interior block; with
(2) at least one aldehyde source and at least one other phenolic monomeric compound having formula (III):

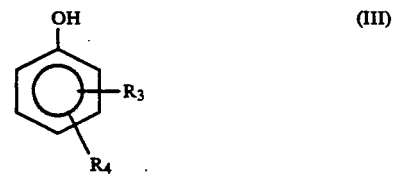

wherein $R_3$ and $R_4$ are individually selected from the group consisting of hydrogen, lower alkyl having 1–4 carbon atoms, halogen, and hydroxyl; wherein said block phenolic oligomer units constitute from about 5% to about 70% by weight of said binder resin; and wherein the amount of said o-quinonediazide compound or compounds being about 5% to about 40% by weight and the amount of said binder resin being about 60% to 95% by weight, based on the total solids content of said radiation-sensitive composition.

12. The coated substrate of claim 11 wherein said substrate comprises one or more compounds selected from the group consisting of polyester, polyolefin, silicon, gallium arsenide, silicon/silicon dioxide, doped silicon dioxide, silicon nitride, aluminum/copper mixtures, tantalum, copper and polysilicon.

13. The coated substrate of claim 11 wherein said substrate is a silicon wafer coated with silicon dioxide.

* * * * *